US012560615B2

(12) United States Patent
Gharibzadeh et al.

(10) Patent No.: US 12,560,615 B2
(45) Date of Patent: Feb. 24, 2026

(54) BONE TURNOVER MARKERS ADJUSTMENT

(71) Applicants: UNIVERSITEIT GENT, Ghent (BE); IMEC VZW, Leuven (BE); MEDIZINISCHE UNIVERSITAT GRAZ, Graz (AT); ENDOCRINOLOGY AND METABOLISM RESEARCH INSTITUTE, Tehran (IR)

(72) Inventors: Safoora Gharibzadeh, Tehran (IR); Patricia Khashayar, Ghent (BE); Bagher Larijani, Tehran (IR); Peter Hans Dimai, Graz (AT); Barbara Obermayer-Pietsch, Graz (AT)

(73) Assignees: MEDIZINISCHE UNVERSITAT GRAZ, Graz (AT); UNIVERSITEIT GENT, Ghent (BE); ENDOCRINOLOGY AND METABOLISM RESEARCH INSTITUTE, Tehran (IR)

( * ) Notice: Subject to any disclaimer, the term of this patent is extended or adjusted under 35 U.S.C. 154(b) by 687 days.

(21) Appl. No.: 18/012,574

(22) PCT Filed: Jun. 29, 2021

(86) PCT No.: PCT/EP2021/067807
§ 371 (c)(1),
(2) Date: Dec. 22, 2022

(87) PCT Pub. No.: WO2022/002910
PCT Pub. Date: Jan. 6, 2022

(65) Prior Publication Data
US 2023/0236202 A1 Jul. 27, 2023

(30) Foreign Application Priority Data
Jun. 29, 2020 (EP) ..................................... 20182829

(51) Int. Cl.
*G01N 33/68* (2006.01)
*G16H 50/50* (2018.01)

(52) U.S. Cl.
CPC ......... *G01N 33/6887* (2013.01); *G16H 50/50* (2018.01); *G01N 2333/78* (2013.01); *G01N 2333/916* (2013.01); *G01N 2800/10* (2013.01)

(58) Field of Classification Search
CPC ......... G01N 2333/78; G01N 2333/916; G01N 2800/10; G01N 2800/108; G01N 33/6887;
(Continued)

(56) References Cited

U.S. PATENT DOCUMENTS

2009/0299769 A1* 12/2009 Dam ...................... G16H 30/20
382/128
2018/0247020 A1* 8/2018 Itu .......................... G16H 10/60

FOREIGN PATENT DOCUMENTS

CN 111007170 A * 4/2020 .............. A61P 19/10

OTHER PUBLICATIONS

Massera D et al: "Biochemical markers of bone turnover and risk of incident hip fracture in older women: the Cardiovascular Health Study", Osteoporosis International, Springer, GB, Jun. 21, 2019, vol. 30, No. 9, pp. 1755-1765.
Namaste ML et al: "Methodologic approach for the Biomarkers Reflecting Inflammation and Nutritional Determinants of Anemia (BRINDA) project 11", American Journal of Clinical Nutrition, Jun. 14, 2017, vol. 106, No. suppl 1, pp. 333S-347S.
(Continued)

*Primary Examiner* — Jennifer Wecker
(74) *Attorney, Agent, or Firm* — Workman Nydegger

(57) ABSTRACT
A method is for correcting a concentration of a bone turnover marker to obtain an adjusted value which gives an indication of an individual's bone health status or amount of changes occurred over time or by treatment while eliminating the influence of possible pre-analytical variability. The method includes: obtaining the concentration of the bone turnover marker of a sample; correcting the obtained con-
(Continued)

centration using a mathematical model which comprises at least three factors, different from the bone health status, such that for the adjusted value variabilities in the concentration of the bone turnover marker, that are caused by the at least three factors, are substantially filtered out by the mathematical model.

11 Claims, 3 Drawing Sheets

(58) Field of Classification Search
CPC .... G01N 33/6893; G16H 50/20; G16H 50/30; G16H 50/50
See application file for complete search history.

(56) References Cited

OTHER PUBLICATIONS

Vilaca et al: "Bone Turnover Markers: Use in Fracture Prediction", Journal of Clinical Densitometry: Assessment & Management of Musuloskeletal Health, Jul. 17, 2017, vol. 20, No. 3, pp. 346-352.
Zhao et al: "Association between serum levels of bone turnover markers and bone mineral density in men and women with type 2 diabetes mellitus", Journal of Clinical Laboratory Analysis., Nov. 15, 2019, vol. 34, No. 4, pp. 1-11.
Extended European Search Report from corresponding European Patent Application No. EP 20182829.0, Jan. 18, 2021.
International Search Report from corresponding PCT Application No. PCT/EP2021/067807, Oct. 8, 2021.

* cited by examiner

100

200

BONE TURNOVER MARKERS ADJUSTMENT

FIELD OF THE INVENTION

The invention relates to the field of bone related diseases. More specifically it relates to methods and devices for analyzing bone turnover markers (BTMs). These may for example be used for screening, diagnosis, and/or monitoring of osteoporosis.

BACKGROUND OF THE INVENTION

Bone is a dynamic tissue with constant remodeling during the lifetime. This continuous remodeling of bone is a combination of bone formation and resorption at various rates. With the ageing population in most countries, disorders of bone and mineral metabolism are becoming increasingly relevant to every day clinical practice. Consequently, the interest in, and the need for effective measures to be used in the screening, diagnosis and follow-up of such pathologies has markedly grown. Together with clinical and imaging techniques, biochemical tests play an important role in the assessment and differential diagnosis of metabolic bone disease.

BTMs are chemical compounds whose presence can be detected in body fluids such as but not limited to serum, plasma, or urine, and who ideally reflect bone turnover, i.e. resorption, formation or combinations of both. BTMs reflect changes in bone metabolism more rapidly than changes in other clinical test such as bone mineral density and could potentially be used as indicators in the diagnosis and monitoring of metabolic bone diseases. Changes of bone turnover with aging are responsible for bone loss and play a major role in osteoporosis. Although unquestionably valuable tools, their use in clinical practice are challenged by two sources of variability: pre-analytical and analytical. Little is known about the pre-analytical precautions for their correct use; moreover, biological variability will affect pre-analytical variability and this may be very important in elderly, in whom several co-existing factors may influence the level of BTMs.

Before using these markers in clinical practice, they need to be adjusted for the influential factors. This will allow diagnosing patients at risk of developing osteoporosis ought to elevated serum bone-turnovers in osteoporotic patients.

There is therefore a need for methods and devices which capture the effect of these factors.

SUMMARY OF THE INVENTION

It is an object of embodiments of the present invention to provide a good method and device for analyzing BTMs.

The above objective is accomplished by a method and device according to the present invention.

In a first aspect embodiments of the present invention relate to a method for correcting a concentration of a bone turnover marker to obtain an adjusted concentration, eliminating the effect of pre-analytical variability, which gives an indication of an individual's bone health status or amount of changes, occurred over time or by treatment.

The method comprises:
obtaining the concentration of the bone turnover marker of a sample,
correcting the concentration of the bone turnover marker using a mathematical model which comprises at least three factors, different from the bone health status, wherein the model is obtained such that for the corrected value variabilities in the concentration of the bone turnover marker, that are caused by the at least three factors, are substantially filtered out by the mathematical model. Thus an indication corresponding with the patients' actual osteoporosis status can be obtained.

It is an advantage of embodiments of the present invention that the negative influence of possible preanalytical variability is eliminated from the corrected bone turnover marker.

In a second aspect embodiments of the present invention relate to a device which is configured for executing such a method. Such a device may for example be used as a point-of-care device.

It is an advantage of embodiments of the present invention that for a specific type of biomarkers, which is mainly related to osteoporosis, a normalized value can be obtained that filters out the variabilities influencing the biomarker that are separate from the disease, in order to introduce an absolute scale on which this normalized value indicates whether there is a problem or not. For example, an absolute scale may no longer be dependent on ethnicity, age, time of day for sample collection, fasting status at time of sample collection, etc.).

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
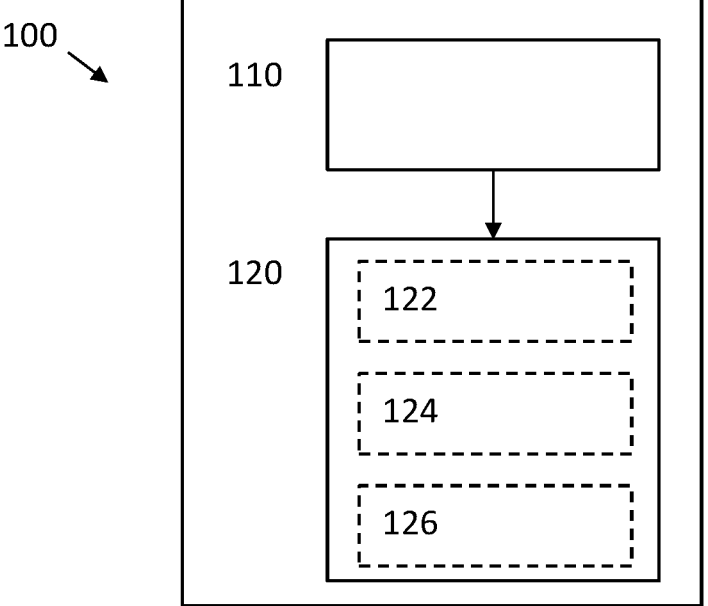
FIG. 1 shows a flow chart of a method in accordance with embodiments of the present invention.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In a first aspect embodiments of the present invention relate to a method 100 for correcting a concentration of a bone turnover marker to obtain an adjusted value, such that for the adjusted value variabilities in the concentration of the bone turnover marker, that are caused by the at least three factors, are substantially filtered out. Thus an adjusted value is obtained which gives an indication of an individual's bone health status or amount of changes occurred over time or by treatment.

The method 100 comprises:

obtaining 110 the concentration of the bone turnover marker of a sample, correcting 120 the concentration of the bone turnover marker using a mathematical model which comprises at least three factors, different from the bone health status, such that for the adjusted value variabilities in the concentration of the bone turnover marker, that are caused by the at least three factors, are substantially filtered out by the mathematical model. It is thereby an advantage of embodiments of the present invention that the corrected bone turnover marker gives an indication corresponding with the patients' actual BTM level, eliminating the effect of possible pre-analytical variabilities.

An example of such a method is schematically illustrated in FIG. 1.

The model may be obtained for a known database of patient data. The model may give an indication of the amount of changes caused by treatment or patient's health status for the database of patient data The advantage of such a method 100 is that the adjusted BTM is less sensitive to the factors which are present in the model, and has better prognostic value to long term changes.

In embodiments of the present invention one or more of the following BTMs may be corrected: serum bone—specific alkaline phosphatase (bALP), serum osteocalcin (Oc), serum type 1 procollagen (P1NP), serum collagen btype 1 cross-linked C-telopeptide (CTx), and tartrate-resistant acid phosphatase 5*b* (TRAP). The BTMs of a sample may be obtained by measurement.

Examples of factors are the specimen and mode of sample collection, the circadian rhythm, and uncontrollable clinical risk factors.

At least three factors may be selected from the list which comprises age, smoking, alcohol, history of fracture, osteoporosis related drugs, physical activity, taking corticosteroids for more than three months, renal disease, liver disease, type 2 diabetes mellitus, thyroid disorder, menopausal status, menstrual cycle, years after menopause, gender, blood sampling time (circadian rhythm) and fasting status at the time of sample collection.

In some embodiments of the present invention, blood sampling time and fasting are factors which are selected by default. In such embodiments, the bone turnover marker is corrected for the time of the day when the sample was taken as well as the individual's fasting status.

The number of factors in the model may be limited, the advantage thereof being that the sparse data problem can be avoided. The factors may for example only be selected from the predefined list of factors.

To avoid sparsity some factors may be omitted from the predefined list. Alcohol, liver and renal diseases may for example be omitted in some models. Smoking may for example be omitted from the women's model. Thyroid disorder may for example be omitted from the men's model.

The maximum number of factors may for example be 16. This could be the case if the factors are solely selected from the predefined list of factors.

According to different determinants of pre analytical variability in men and women, the models may be developed for men and women, separately.

In embodiments of the present invention, the measured BTMs may be adjusted in three steps:

correcting 122 the BTM using a correction factor for the difference between capillary and venous blood;

correcting 124 for the circadian and fasting effect (the time of blood sampling);

correcting 126 for uncontrollable clinical risk factors.

These steps may be executed in the order as specified above or in another order. Therefore in FIG. 1 no arrows are present to indicate an order in which the steps should be executed.

Circadian rhythms may be various in different populations. A systematic review and meta-analysis on a known database of normal population may be done to estimate the circadian rhythm of BTMs in men and women.

International databases including Medline, Embase, Web of Sciences, Scopus, and a database from the Bushehr Elderly Health (BEH) may be searched. Any other available database (e.g. available in literature) of patient data which gives information on the patients' BTM levels may be used. A subset of patient data may be selected.

The units of measurements of different databases may be converted to a unique unit to make merging the information possible.

In the following paragraph, the effect of circadian rhythm for different BTMs is illustrated using illustrative graphs. These graphs are obtained by meta-analysis. The invention is not limited to these graphs. Depending on the analysis, other graphs may be obtained.

Figure 3:
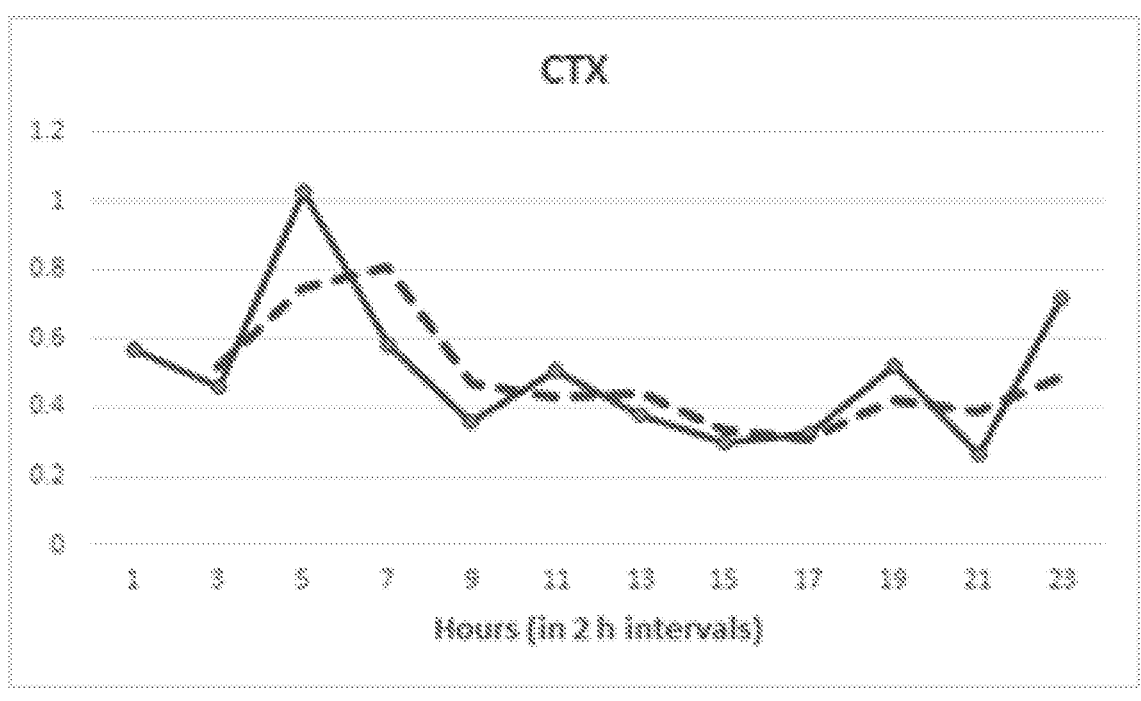
FIG. 3 shows the diurnal trend of CTX in ng/ml.

FIG. 3 shows the diurnal trend of CTX in ng/ml. In this and the following figures, the fixed line shows the observed data and the dashed line shows the moving average.

Figure 4:
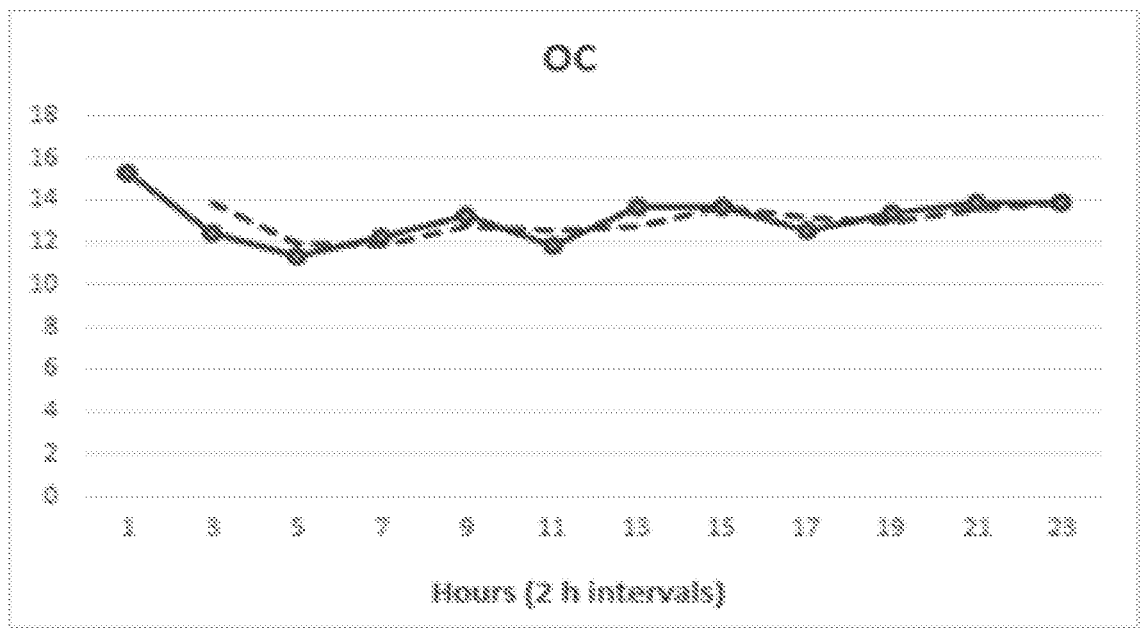
FIG. 4 shows the diurnal trend of OC in ng/ml.

FIG. 4 shows the diurnal trend of OC in ng/ml.

Figure 5:
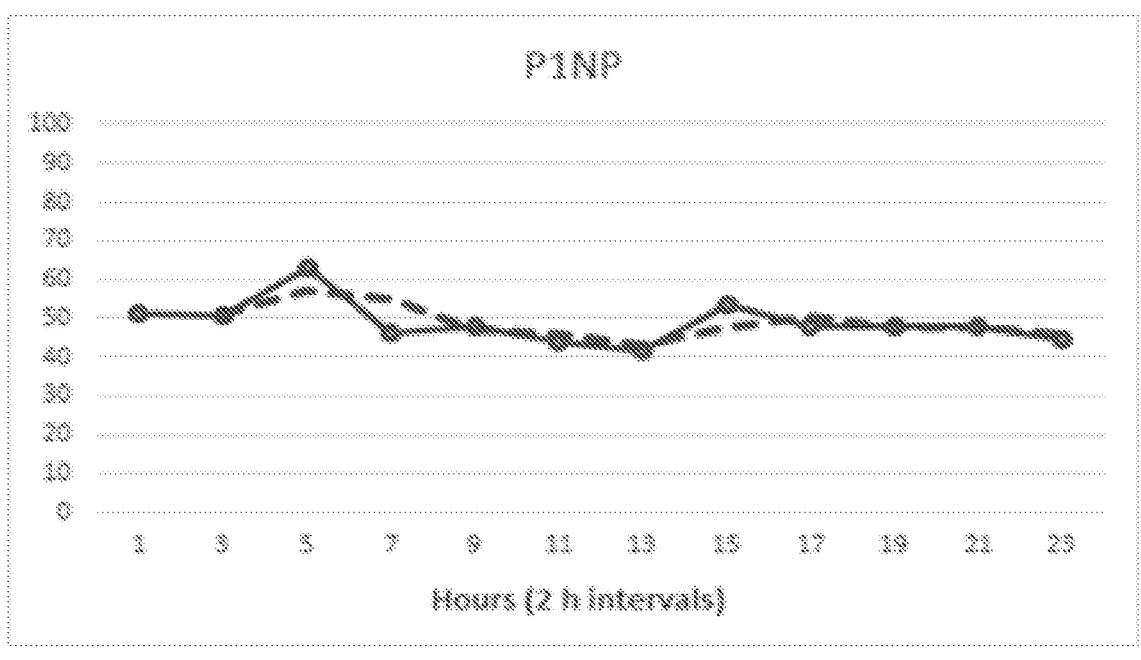
FIG. 5 shows the diurnal trend of P1NP in ng/ml.

FIG. 5 shows the diurnal trend of P1NP in ng/ml.

Figure 6:
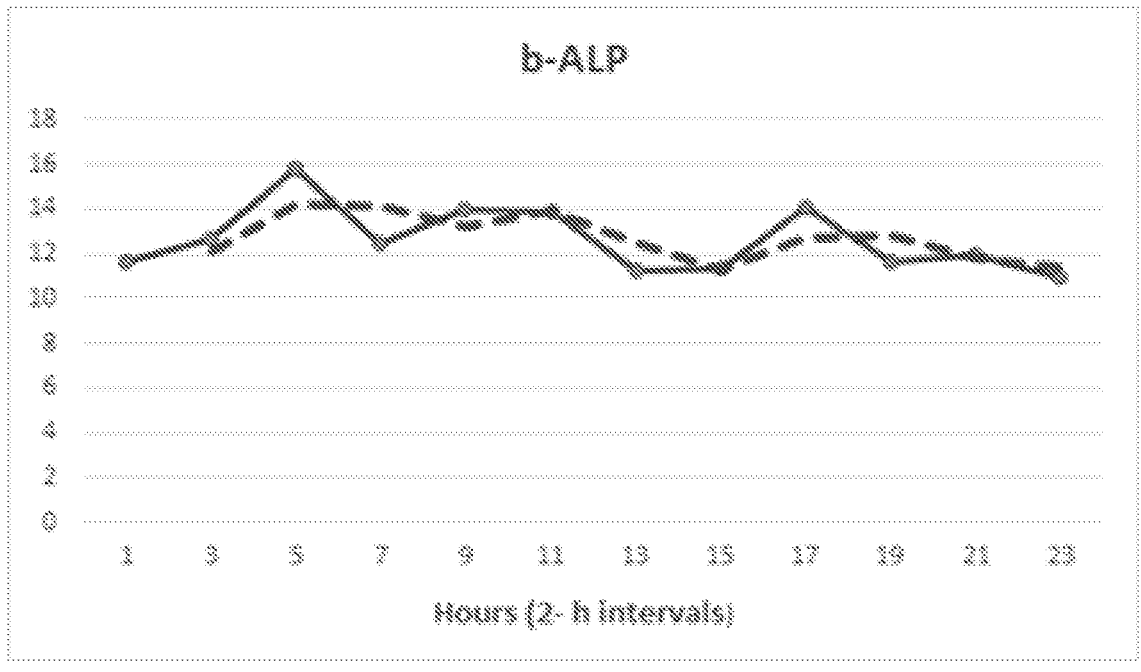
FIG. 6 shows the diurnal trend of bone-ALP in ng/ml.

FIG. 6 shows the diurnal trend of bone-ALP in ng/ml.

Correction factors for adjusting a BTM can be obtained for different time intervals to adjust for the circadian rhythm. This may be the factor "a" in the following equation:

$$BTM'=a*BTM$$

$$BTM''=b*BTM'$$

The factor b may be used for correcting for the blood sample type. The ratio of the venous to capillary blood sample of a number of participants may be calculated and averaged. In other words, levels of each BTM is first measured in the blood collected from each patient's vein and capillary. These numbers are then divided to each other to calculate the ratio and lastly the average ratio is calculated for the subset.

These formulas represent one way of compensating for the circadian rhythm and for the blood sample type. The invention is, however, not limited thereto.

It is found by the inventors that the most influential preanalytical variability factors are: age, pregnancy/lactation, systemic inflammatory disease (IBD, RA, COPD), gender, recent fractures (up to one year), renal impairment (GFR<20 ml/min/1.73 m$^2$), ethnicity, glucocorticoids, liver disease, immobility/loss of gravity (bed rest, space flight), oral contraception, thyroid disease, exercise, diet, diabetes.

In embodiments of the present invention, each factor in the model has a specific weight and the weight for each factor may be determined given a database of patient data.

This weight represents the variable importance and may be obtained by analyzing the variability of BTMs and changes during measurements. The weight represents how much a given model uses that variable to make accurate predictions.

Using regression analysis factors associated with the preanalytical variability of BTMs may be determined as well as the strength and direction of these associations.

Regression analysis is a statistical tool that allows to estimate the mathematical relationship between a dependent variable (usually called y or response) and an independent variable (usually called x, predictor or regressor).

$$Y=\beta_0+\beta_1x_1+\beta_2x_2+\ldots+\oplus_kX_k$$

$\beta_0$=constant of the line, $\beta_i$=slope of the variable, Y refers to the BTM, and the factors $x_i$ refer to the preanalytical factors. A multiple regression model with k independent variables fits a regression "surface" in k+1 dimensional space.

In embodiments of the present invention the coefficients may be obtained by the least square method. The least squares function is given by:

$$L = \sum_{i=1}^{n}\varepsilon_i^2 = \sum_{i=1}^{n}\left(y_i - \beta_0 - \sum_{j=1}^{k}\beta_jx_{ij}\right)^2$$

The least squares estimates must satisfy:

$$\frac{\partial L}{\partial \beta_0}\bigg|_{\hat{\beta}_0, \hat{\beta}_1, \ldots, \hat{\beta}_k} = -2\sum_{i=1}^{n}\left(y_i - \hat{\beta}_0 - \sum_{j=1}^{k}\hat{\beta}_jx_{ij}\right) = 0$$

And:

$$\frac{\partial L}{\partial \beta_j}\bigg|_{\hat{\beta}_0, \hat{\beta}_1, \ldots, \hat{\beta}_k} = -2\sum_{i=1}^{n}\left(y_i - \hat{\beta}_0 - \sum_{j=1}^{k}\hat{\beta}_jx_{ij}\right)x_{ij} = 0$$

Outliers are values that are spaced from the rest of the data. The median absolute deviation (MAD) method may be used to detect outliers for a BTM. MAD is one of the basic robust methods which are largely unaffected by the presence of extreme values of the dataset. Median +/−3*MAD may for example be used as an indication of being an outlier. Outliers may be caused by an error in recording the value or may be the result of a measurement error. If, however, this is not the case the outliers are valid observations. Preferably such outliers in the response variable should be retained in the model. In embodiments of the present invention, the coefficients may be obtained using a regression model using resistant procedures when outliers are reported.

Therefore, robust regression methods may be used to retain the outliers in the model. Robust regression methods provide an alternative to least squares regression by requiring less restrictive assumptions. These methods attempt to dampen the influence of outlying cases in order to provide a better fit to the majority of the data. Examples thereof are: the least median squares estimator (LMS), the least trimmed squares estimator (LTS), the S-estimator (S), the least absolute value estimator (LAV), the Huber's M-estimator, the Tukey's M-estimator, or the Hampel's M-estimator. Tukey's M-estimator gave the lowest total absolute bias and total MSE values in simulation studies. Hampel's M-estimators gave lower bias and MSE values in real data studies. Hence, Tukey's and Hampel's M-estimators are preferential estimators for obtaining a model to be used in a method and device according to embodiments of the present invention.

In embodiments of the present invention multiplicative correction factors corresponding to a plurality of preanalytical factors may be found. The logarithm of BTMs may be modelled.

A regression estimator with a high breakdown point may be achieved.

To measure the strength of the linear relationship, the measure of determination may be used. R-squared is a measure of explanatory power of the model.

$$0 \leq R^2 \leq 1$$

R-squared measures the proportion of the variation in y that is predictable by the x.

Multicollinearity occurs when two or more covariates are highly correlated with each other. It affects the inferences about the significance of the collinear variables. It affects the coefficients estimate and reduces the statistical power of the models.

In embodiments of the present invention variance Inflation Factors (VIFs) may be used to detect multicollinearity among predictors in a multiple linear regression model. Mean (VIF)>1 reflects multicollinearity of variables. In case of multicollinearity variables the correlation may be checked, highly correlated variables may be removed or the variables may be centered and the regression re-run. Cross-validation method may be used to control over the fitness of the model.

One of the main assumptions for the regression analysis is the homogeneity of variance of the residuals. In embodiments of the present invention, the Breusch-Pagan test may be used to check the homogeneity of variance of the residuals.

In case of heteroscedasticity robust standard errors estimation may be used the assumption may be re-checked using White's test. The Box-Cox transformation may be used in case of the heteroscedasticity.

In sex specific robust multiple linear regression, adjustment may for example be done for age, smoking, alcohol, history of fracture after the age of 45, drugs, physical activity, taking corticosteroids for more than three months, renal disease, liver disease, T2DM, Thyroid disorder, menopausal status, and years after menopause. Years after menopause may be divided into two categories: less than 10 years as early post menopause and more than 10 years as late post menopause.

To increase the overall power of the models, the effects of age and body mass index (BMI) may be detected by natural cubic splines.

In embodiments of the present invention the effect of each variable may be measured by the exponential of its regression coefficient. The aim of this modelling is to find multiplicative correction factors corresponding to each of the preanalytical factors. In such embodiments the model may comprise the following adjustment:

$$y = y_0 (e^{\beta_1 X_1})(e^{\beta_2 X_2}) \dots (e^{\beta_k X_k}) = y_0 e^{\Sigma_i \beta_i X_i},$$

Wherein y is the adjusted bone turnover marker, $y_0$ is the mean-measured bone turnover marker across all patients in a database, $\beta_i$, is the estimated coefficient for factor $x_i$, given the database, and k is the number of factors.

In that case:

$$\ln(y) = \ln(y_0) + \sum_i \beta_i x_i \text{ or } \ln\left(\frac{y}{y_0}\right) = \sum_i \beta_i x_i.$$

For instance, if the smoking status of a 65-year-old male changes between two consecutive follow-ups (given that the other factors do not change), the ratio of these two measurements equals to:

$$\frac{y_t}{y_{t+1}} = e^{\beta_{smoking}}$$

In embodiments of the present invention the model may comprise the following adjustment:

$$BTM = \left(e^{\beta_0}\right)\left(e^{\beta_1 * Age}\right)\left(e^{\beta_2 * BMI}\right)\left(e^{\beta_3 * smoking}\right)$$
$$\left(e^{\beta_4 * Alcohol}\right)\left(e^{\beta_5 * taking-steroids}\right)\left(e^{\beta_6 * history-of-fracture}\right)\left(e^{\beta_7 * T2DM}\right)$$
$$\left(e^{\beta_8 * OP\_drugs}\right)\left(e^{\beta_9 * thyroid\_disease}\right)\left(e^{\beta_{10} * Liver\_disease}\right)\left(e^{\beta_{11} * Kidney\_disease}\right)$$
$$\left(e^{\beta_{12} * mentrual\_cycle}\right)\left(e^{\beta_{13} * menopausal\_status}\right)\left(e^{\beta_{14} * physical\_activity}\right)\left(e^{\beta_{15} * Fasting}\right)$$

8

In an exemplary embodiment of the present invention the mathematical model for correcting the BTM may be as follows:

$$BTM = \left(e^{\beta_0}\right)\left(e^{\beta_1 * Age}\right)\left(e^{\beta_2 * BMI}\right)\left(e^{\beta_3 * smoking}\right)$$
$$\left(e^{\beta_4 * Alcohol}\right)\left(e^{\beta_5 * taking-steroids}\right)\left(e^{\beta_6 * history-of-fracture}\right)\left(e^{\beta_7 * T2DM}\right)$$

After developing the model, to check the validity of the estimated model, different measures of diagnostics may be used. Some of the assumptions that may be checked in the regression are: multicollinearity, homogeneity of variance, and linearity. Based on the results the final model may be developed.

For example, the final equation for OC in men may be modelled as:

$$OC = 21.33 * \left(e^{0.07 * Age_{<70}}\right)\left(e^{0.11 * Age_{70-80}}\right)\left(e^{0.20 * Age_{>=80}}\right)$$
$$\left(e^{-0.08 * BMI_{<25}}\right)\left(e^{0.07 * BMI_{25-30}}\right)\left(e^{0.25 * BMI_{>=30}}\right)\left(e^{0.07 * smoking}\right)$$
$$\left(e^{0.03 * taking-steroids}\right)\left(e^{0.1 * history-of-fracture}\right)\left(e^{-0.26 * T2DM}\right)\left(e^{0.01 * PhA}\right)$$

The above equation may be clarified, with the following hypothetical scenarios. A 67-year-old man physically inactive, with a past medical history of thyroid disease, BMI equals to 26, and negative history of T2DM and taking corticosteroids, attended to a clinic for the first time.

Summary of patient's variables is as:

| Age(60-70) | Thyroid = 1 | Alcohol = 0 | Smoking = 0 |
| --- | --- | --- | --- |
| PhA = 0 | BMI (25-30) | Taking steroids = 0 | T2DM = 0 |

Between two consecutive follow ups, his diabetes status changes to 1 and clinician observe an OC equal to 22 for this patient, to adjust for the effect of this change the clinician should multiply the observed level by exp (−0.25)=0.78:

Corrected level=measured level* exp(0.08)=22*0.87=17.13

Between two consecutive follow ups, the patient's BMI decreases to 24 (transferred to a <25 category), and OC=22

Corrected level=measured level* exp(−0.25)=22*1.08=23.83

More than one change may be combined: for a measured value of 22, a physically active patient, a T2DM (+), and a decrease in BMI, the following correction may be applied:

Corrected level=22*1.01*0.87*1.08=20.87

In another exemplary embodiment of the present invention the correction for the P1NP for women may be modelled as follows:

$$P1NP = 35.87 * \left(e^{0.15 * Age_{50-60}}\right)\left(e^{0.10 * Age_{60-70}}\right)$$
$$\left(e^{0.16 * Age_{\geq 70}}\right)\left(e^{-0.23 * BMI_{<25}}\right)\left(e^{-0.38 * BMI_{25-30}}\right)\left(e^{-0.18 * BMI_{>=30}}\right)$$
$$\left(e^{0.05 * smoking}\right)\left(e^{-0.05 * Alcohol}\right)\left(e^{-0.07 * history-of-fracture}\right)\left(e^{-0.17 * T2DM}\right)$$
$$\left(e^{0.03 * thyroid\_disease}\right)\left(e^{-0.03 * PhA}\right)\left(e^{0.25 * early-menopause}\right)\left(e^{0.09 * late-menopause}\right)$$

Below some examples for correcting the P1NP are given. A 59 year-old-woman, physically active, with negative past medical history of thyroid disease and diabetes, a BMI equals to 22, and negative history of taking corticosteroids, attended to a clinic for the first time.

After one year, some factors are changed. She becomes physically inactive, her age=60 and she has a measured P1NP of 38. Using the formula, the following corrected level can be obtained.

$$Corrected\ level =$$
$$measure\ level * effect\ of\ physical\ activity * effect\ of\ age =$$
$$38 * exp(-0.03) * exp(0.10) = 40.75$$

In the following table the effects of pre-analytical factors on the level of osteocalcin in women are illustrated. Only a limited number of factors are selected by the inventors.

| | Model parameters | Variable importance |
|---|---|---|
| R-Squared | 0.23* | |
| Age‡ | | 0.32 |
| 60-70 | 1.43* | |
| 70-80 | 1.58* | |
| >=80 | 1.69* | |
| BMI‡ | | 0.09 |
| <25 | 0.97 | |
| 25-30 | 0.65 | |
| >=30 | 0.69 | |
| Alcohol | | |
| Smoking Status (0/1) | 1.05 | 0.00 |
| Physical Activity (0/1) | 0.98 | 0.03 |
| Taking Corticosteroid more than 3 months | 0.99 | 0.00 |
| History of fracture | 0.92 | 0.02 |
| Thyroid Disease | 1.01 | 0.00 |
| T2DM | 0.70* | 0.50 |
| Menopausal status | | 0.01 |
| Peri-menopause | | |
| Early menopause** | | ref |
| Late menopause(ref) | 0.91 | |

**years since menopause less than 10 years considered as early menopause,
‡these cut points are breakdown points(knots) in splines.

The values in the column "variable importance" are based on the Pratt formula:

$$variable\ importance = \frac{\hat{\beta}\hat{\rho}}{R^2}$$

where p denotes the estimate of Pearson's product moment correlation between the predictor and the dependent variable, and β denotes the standardized regression coefficient Thus, in an exemplary embodiment of the present invention the following model may be used for correcting the effect of pre-analytical factors on the level of osteocalcin in women:

$$ln(OC_{Women})=3.10+1.43*Age_{60-70}+1.58*Age_{70-80}+$$
$$1.69*Age_{>80}+0.97*BMI_{<25}+0.65*BMI_{25-30}+$$
$$0.69*BMI_{>30}+1.05*Smoking\_Status+0.98*PhA+$$
$$0.99*taking\_GC+0.92*fxhist+$$
$$1.01*Thyroid\_isease+0.70*T2DM+$$
$$0.91*Late\_Menopause$$

In the models of this patent application the following logic is applied for the factors. $Age_{60-70}$ represents a binary value which is 1 if the age is between 60 and 70 and 0 if the age is larger than or equal to 70 and smaller than 60. $Age_{>80}$ represents a binary value which is 1 if the age is larger than 80 years, and 0 it is smaller than or equal to 80. $BMI_{<25}$ represents a binary value which is 1 if the BMI is smaller than 25 and 0 if the BMI is larger than or equal to 25. $BMI_{25-30}$ represents a binary value which is 1 if the BMI is between 25 and 30 and 0 if the BMI is larger than or equal to 30 and smaller than 25. $BMI_{>30}$ represents a binary value which is 1 if the BMI is larger than 30 and 0 if the BMI is smaller than or equal to 30. The same logic can be applied to other factors in which the subscript defines a range. Smoking_Status is a binary value which is 0 for a non-smoker and 1 for a smoker. PhA is 0 for a person which is physically inactive and 1 for a person which is physically active. Taking_GC is 1 for a person who is taking Corticosteroid for a period of more than 3 months. Fxhist represents a binary value which is 1 in case of a recent fracture (e.g. less than one year ago, e.g. only for a person older than 45y) and 0 in case of no recent fracture. "Thyroid disease" is 1 for a person with thyroid disorder and 0 for a person without thyroid disorder. T2DM is 1 in case of type 2 diabetes and 0 if not. "Late Menopause" is 1 in case of 10 or more years since menopause and 0 in case of less than 10 years since menopause. This is the referencing used for this model. Depending on the model factors may be added or removed from this list.

The invention is not limited to this model and depending on the database used (e.g. for a different population) and on the factors used another model may be obtained. An example thereof is given below:

$$ln(OC_{women})=3.15+1.12*Age_{50-60}+1.44*Age_{60-70}+$$
$$1.20*Age_{70-80}+0.71*BMI_{<25}+0.63*BMI_{25-30}+$$
$$0.81*BMI_{>30}+0.97*Alcohol+1.05*$$
$$Smoking\_Status+0.96*PhA+0.93*fxhist+$$
$$1.02*Thyroid\_Disease+0.90*T2DM+1.18*ear-$$
$$ly\_meopause+1.03*Late\_Menopause$$

In the following table the effects of pre-analytical factors on the level of osteocalcin in men are illustrated. Only a limited number of factors are selected by the inventors.

| | Model parameters | Variable importance |
|---|---|---|
| R-squared | 0.11 | |
| Age‡ | | 0.08 |
| 60-70 | 1.08 | |
| 70-80 | 1.12 | |
| >=80 | 1.23 | |
| BMI‡ | | 0.06 |
| <25 | 0.92 | |
| 25-30 | 1.08 | |
| >=30 | 1.29 | |
| Alcohol | | |
| Smoking Status (0/1) | 1.08 | 0.03 |
| Physical Activity (0/1) | 1.00 | 0.02 |
| Taking Corticosteroid more than 3 months | 1.03 | 0.02 |
| History of fracture | 1.10 | 0.04 |
| Thyroid Disease | | |
| T2DM | 0.77* | 0.74 |
| Menopausal status | | |
| Peri-menopause | | |
| Early menopause** | | |
| Late menopause(ref) | | |

In the following table the effects of pre-analytical factors on the level of CTX in men are illustrated. Also, in this case only a limited number of factors are selected by the inventors.

| | Model parameters | Variable importance |
|---|---|---|
| R-squared | 0.19* | |
| Age‡ | | 0.17 |
| 60-70 | 1.12 | |
| 70-80 | 1.07 | |
| >=80 | 1.50* | |
| BMI‡ | | 0.04 |
| <25 | 1.09 | |
| 25-30 | 1.30 | |
| >=30 | 1.36 | |
| Alcohol | | |
| Smoking Status (0/1) | 1.16* | 0.06 |
| Physical Activity (0/1) | 1.21* | 0.10 |
| Taking Corticosteroid more than 3 months | 1.04 | 0.00 |
| History of fracture | 1.15* | 0.03 |
| Thyroid Disease | | |
| T2DM | 0.68* | 0.59 |

Thus, in an exemplary embodiment of the present invention the following model may be used for correcting the effect of pre-analytical factors on the level of CTX in men:

$$\ln(CTX_{men})=1.04+1.12*Age_{60-20}+1.07*Age_{70-80}+$$
$$1.50*Age_{>80}+1.09*BMI_{<25}+1.30*BMI_{25-30}+$$
$$1.36*BMI_{>30}+1.16*Smoking\_Status+1.21*PhA+$$
$$1.04*taking\_GC+1.15*fxhist+0.68*T2DM$$

In the following table the effects of pre-analytical factors on the level of CTX in women are illustrated. Also, in this case only a limited number of factors are selected by the inventors.

| | Model parameters | Variable importance |
|---|---|---|
| R-squared | 0.20* | |
| Age‡ | | 0.26 |
| 60-70 | 1.28 | |
| 70-80 | 1.63 | |
| >=80 | 1.83* | |
| BMI‡ | | 0.07 |
| <25 | 0.80 | |
| 25-30 | 0.92 | |
| >=30 | 0.94 | |
| Alcohol | | |
| Smoking Status (0/1) | 1.10 | 0.04 |
| Physical Activity (0/1) | 0.92 | 0.02 |
| Taking Corticosteroid more than 3 months | 1.01 | 0.00 |
| History of fracture | 0.99 | 0.00 |
| Thyroid Disease | 1.06 | 0.00 |
| T2DM | 0.72* | 0.54 |
| Menopausal status | | 0.04 |
| Peri-menopause | | |
| Early menopause* | Ref | |
| Late menopause | 0.85 | |

**years since menopause less than 10 years considered as early menopause,
‡these cut points are breakdown points(knots) in splines.

Thus, in an exemplary embodiment of the present invention the following model may be used for correcting the effect of pre-analytical factors on the level of CTX in women:

$$\ln(CTX_{women})=1.34+1.28*Age_{60-70}+1.63*Age_{70-80}+$$
$$1.83*Age_{>80}+0.8*BMI_{<25}+0.92*BMI_{25-30}+$$
$$0.94*BMI_{>30}+1.10*Smoking\_Status+0.92*PhA+$$
$$0.00*taking\_GC+0.99*fxhist+0.72*T2DM+$$
$$0.85*late\_Menopause$$

In the following table the effects of pre-analytical factors on the level of b-ALP in men are illustrated. Also in this case only a limited number of factors are selected by the inventors.

| | Model parameters | Variable importance |
|---|---|---|
| R-squared | 0.04 | |
| Age ‡ | | 0.50 |
| 60-70 | 1.08 | |
| 70-80 | 0.90 | |
| >=80 | 1.15 | |
| BMI ‡ | | 0.19 |
| <25 | 1.18 | |
| 25-30 | 1.70 | |
| >=30 | 1.18 | |
| Alcohol | | |
| Smoking Status (0/1) | 1.00 | 0.02 |
| Physical Activity (0/1) | 1.08 | 0.07 |
| Taking Corticosteroid more than 3 months | 1.07 | 0.05 |
| History of fracture | 1.08 | 0.01 |
| Thyroid Disease | | |
| T2DM | 0.94 | 0.13 |

Thus, in an exemplary embodiment of the present invention the following model may be used for correcting the effect of pre-analytical factors on the level of b-ALP in men:

$$\ln(bALP_{men})=2.45+1.08*Age_{60-70}+0.90*Age_{70-80}+$$
$$1.15*Age_{>80}+1.18*BMI_{<25}+1.70*BMI_{25-30}+$$
$$1.18*BMI_{>30}+1.00*Smoking\_Status+1.08*PhA+$$
$$1.07*taking\_GC+1.08*fxhist+0.94*T2DM$$

In the following table the effects of pre-analytical factors on the level of b-ALP in women are illustrated. Also in this case only a limited number of factors are selected by the inventors.

| | Model parameters | Variable importance |
|---|---|---|
| R-squared | 0.07 | |
| Age ‡ | | 0.41 |
| 60-70 | 0.79 | |
| 70-80 | 1.28 | |
| >=80 | 1.60 | |
| BMI ‡ | | 0.07 |
| <25 | 1.06 | |
| 25-30 | 1.20 | |
| >=30 | 1.20 | |
| Alcohol | | |
| Smoking Status (0/1) | 1.05 | 0.02 |
| Physical Activity (0/1) | 1.05 | 0.01 |
| Taking Corticosteroid more than 3 months | 0.93 | 0.09 |
| History of fracture | 0.97 | 0.01 |
| Thyroid Disease | 1.06 | 0.05 |
| T2DM | 0.92 | 0.2 |
| Menopausal status | | 0.12 |
| Early menopause* | Ref | |
| Late menopause | 0.92 | |

In the following table the effects of pre-analytical factors on the level of TRAP in women are illustrated. Also in this case only a limited number of factors are selected by the inventors.

In the following table the effects of pre-analytical factors on the level of TRAP in men are illustrated. Also in this case only a limited number of factors are selected by the inventors.

| | Model parameters | Variable importance |
|---|---|---|
| R-squared | 0.06 | |
| Age‡ | | 0.14 |
| 60-70 | 1.13 | |
| 70-80 | 1.07 | |

-continued

| | Model parameters | Variable importance |
|---|---|---|
| >=80 | 1.04 | |
| BMI‡ | | 0.27 |
| <25 | 0.99 | |
| 25-30 | 1.21 | |
| >=30 | 0.90 | |
| Alcohol | | |
| Smoking Status (0/1) | 1.02 | 0.02 |
| Physical Activity (0/1) | 1.10 | 0.31 |
| Taking Corticosteroid more than 3 months | 1.06 | 0.09 |
| History of fracture | 1.09 | 0.15 |
| Thyroid Disease | | |
| T2DM | 0.99 | 0.00 |

In the following table the effects of pre-analytical factors on the level of TRAP in women are illustrated. Also in this case only a limited number of factors are selected by the inventors.

| | Model parameters | Variable importance |
|---|---|---|
| R-squared | 0.08 | |
| Age‡ | | 0.17 |
| 60-70 | 1.04 | |
| 70-80 | 0.97 | |
| >=80 | 1.15 | |
| BMI‡ | | 0.38 |
| <25 | 0.79* | |
| 25-30 | 0.61 | |
| >=30 | 0.82 | |
| Alcohol | | |
| Smoking Status (0/1) | 1.01 | 0.01 |
| Physical Activity (0/1) | 0.93 | 0.05 |
| Taking Corticosteroid more than 3 months | 1.05 | 0.05 |
| History of fracture | 0.97 | 0.00 |
| Thyroid Disease | 0.99 | 0.00 |
| T2DM | 0.92 | 0.22 |
| Menopausal status | | 0.10 |
| Early menopause* | Ref | |
| Late menopause(ref) | 0.92 | |

In a second aspect embodiments of the present invention relate to a device 200 for correcting a bone turnover marker to obtain an adjusted bone turnover marker. Such a device may be a point of care and/or an in-office device. The device comprises:

a module 210 configured for acquiring the bone turnover marker, a processing module 220 for correcting the bone turnover marker using a method in accordance with embodiments of the present invention.

Figure 2:
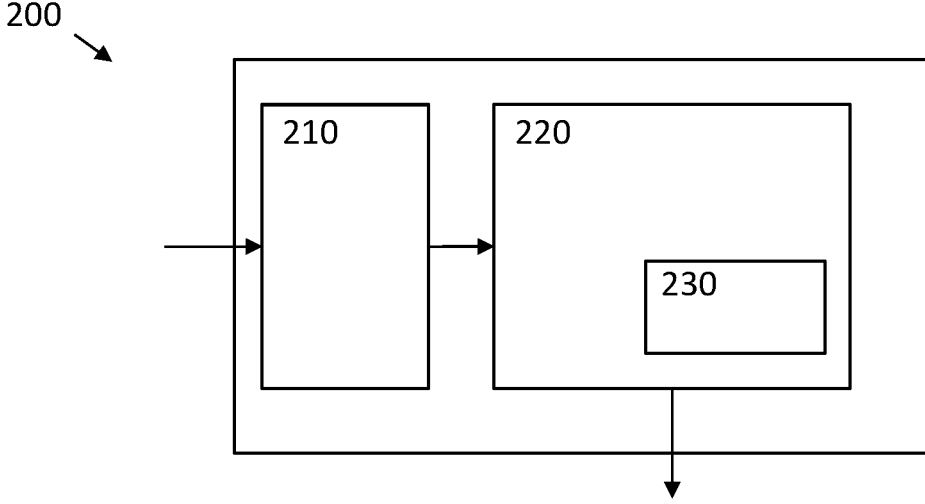
FIG. 2 shows a schematic drawing of a device in accordance with embodiments of the present invention.

A schematic drawing of such a device, in accordance with embodiments of the present invention, is illustrated in FIG. 2.

The adjusted bone turnover marker may give an indication of bone health, high turnover individuals, higher risk of osteopenia/osteoporosis and fracture, and allows to monitor changes during follow-ups.

The processing module 220 may comprise a processing unit configured for executing a computer program product for correcting the bone turnover marker. Different kinds of processing modules may be used such as processors, micro-controllers, or integrated circuits such as field programmable gate arrays (FPGAs) or application-specific integrated circuits (ASICs).

The processing module may comprise a data carrier 230 for storing the computer program product.

In embodiments of the present invention the module 210 configured for acquiring the bone turnover marker may have an interface for inputting the bone turnover marker. This may for example be a keyboard and a display or a touch screen display. This interface or a separate interface may also be used for inputting the factors and the coefficients.

The corrected bone turnover marker may be displayed (e.g. using the display of module 210) or made accessible for the user in any other known way (this is indicated by the outgoing arrow in FIG. 2). It may for example be wirelessly transmitted to a device of the user.

In embodiments of the present invention the module 210 configured for acquiring the bone turnover marker may be a measurement module configured for measuring the bone turnover marker from a sample (e.g. from a blood sample).

In embodiments of the present invention the module 210 configured for acquiring the bone turnover marker may comprise an interface for taking a sample (e.g. using a needle).

The device may for example be configured for utilizing capillary blood samples (e.g. whole blood collected through finger-pricking) for analysis. Alternatively, the device may be configured for utilizing venous blood samples. Depending on the embodiment, the input arrow in FIG. 2 may therefore represent an interface through which a BTM value may be entered, or an interface through which a sample may be entered. In the first case the BTM value is obtained using another device. In the latter case the sample is inserted and the device is configured for measuring a BTM value of the sample.

The invention claimed is:

1. A method for correcting a concentration of a bone turnover marker, selected from the list of serum bone-specific alkaline phosphatase, serum osteocalcin, serum type 1 procollagen, serum collagen type 1 cross-linked C-telopeptide, and tartrate-resistant acid phosphatase 5b, to obtain an adjusted value which gives an indication of an individual's bone health status or amount of changes occurred over time or by treatment, the method comprising:

obtaining the concentration of the bone turnover marker of a sample, correcting the obtained concentration using a mathematical model which comprises at least three factors, different from the bone health status, such that for the adjusted value variabilities in the concentration of the bone turnover marker, that are caused by the at least three factors, are substantially filtered out by the mathematical model;

wherein the at least three factors are selected from a list comprising age, smoking, alcohol, history of fracture, osteoporosis related drugs, physical activity, taking corticosteroids for more than three months, renal disease, liver disease, type 2 diabetes mellitus, thyroid disorder, menopausal status, menstrual cycle, years after menopause, gender, blood sampling time and fasting;

and wherein the model at least comprises the following adjustment:

$$y = y_0(e^{\beta_1 X_1})(e^{\beta_2 X_2}) \ldots (e^{\beta_k X_k}) = y_0 e^{\Sigma_i \beta_i X_i}$$

and wherein y is the adjusted bone turnover marker, $y_0$ is the mean-measured bone turnover marker across all patients in a database, $\beta_i$ is the estimated coefficient for factor xi, and k is the number of factors.

2. The method according to claim 1, wherein two of the selected factors are blood sampling time and fasting.

3. The method according to claim 1, wherein the maximum number of factors in the model is 16.

4. The method according to claim 1, wherein each factor in the model has a specific weight and > wherein the weight for each factor is determined given a database of patient data.

5. The method according to claim 4, wherein the coefficients are obtained via least square method.

6. The method according to claim 5, wherein the weights are obtained using a regression model using resistant procedures.

7. The method according to claim 1, wherein the model at least comprises the following adjustment:

$$BTM = \left(e^{\beta_0}\right)\left(e^{\beta_1 * Age}\right)\left(e^{\beta_2 * BMI}\right)\left(e^{\beta_3 * smoking}\right)$$
$$\left(e^{\beta_4 * Alcohol}\right)\left(e^{\beta_5 * taking-steroids}\right)\left(e^{\beta_6 * history-of-fracture}\right)\left(e^{\beta_7 * T2DM}\right)$$
$$\left(e^{\beta_8 * OP\_drugs}\right)\left(e^{\beta_9 * thyroid\_disease}\right)\left(e^{\beta_{10} * Liver\_disease}\right)\left(e^{\beta_{11} * Kidney\_disease}\right)$$
$$\left(e^{\beta_{12} * mentrual\_cycle}\right)\left(e^{\beta_{13} * menopausal\_status}\right)\left(e^{\beta_{14} * physical\_activity}\right)\left(e^{\beta_{15} * Fasting}\right).$$

8. A device for correcting a bone turnover marker to obtain an adjusted bone turnover marker, the device comprising:

> a module configured for acquiring the bone turnover marker,
>
> a processing module for correcting the bone turnover marker using a method according to claim 1.

9. The device according to claim 8, wherein the module configured for acquiring the bone turnover marker has an interface for inputting the bone turnover marker.

10. The device according to claim 9, wherein the module configured for acquiring the bone turnover marker is a measurement module configured for measuring the bone turnover marker.

11. The device according to claim 10, wherein the module configured for acquiring the bone turnover marker comprises an interface for taking a sample.

\* \* \* \* \*